(12) United States Patent
Stapf et al.

(10) Patent No.: US 7,732,656 B2
(45) Date of Patent: Jun. 8, 2010

(54) MINIMAL CONTACT TREATMENT DEVICE

(75) Inventors: Donald Stapf, Minneapolis, MN (US); Keith J. Leland, Plymouth, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 715 days.

(21) Appl. No.: 10/143,509

(22) Filed: May 10, 2002

(65) Prior Publication Data

US 2002/0169406 A1  Nov. 14, 2002

Related U.S. Application Data

(60) Provisional application No. 60/290,266, filed on May 10, 2001.

(51) Int. Cl.
*A61F 13/00* (2006.01)
*A61F 13/02* (2006.01)
*A61F 15/00* (2006.01)

(52) U.S. Cl. .............. 602/56; 602/41; 602/48; 602/54; 602/55; 602/58; 604/304; 604/305; 604/307

(58) Field of Classification Search ............. 602/41–61; 206/440–441; 604/304, 307, 305, 308
See application file for complete search history.

(56) References Cited

U.S. PATENT DOCUMENTS

| | | | | |
|---|---|---|---|---|
| 4,265,234 A | * | 5/1981 | Schaar | 602/57 |
| 4,334,530 A | * | 6/1982 | Hassell | 602/42 |
| 4,972,829 A | | 11/1990 | Knerr | |
| 5,060,662 A | | 10/1991 | Farnswoth, III | |
| 5,538,500 A | * | 7/1996 | Peterson | 602/48 |
| 5,556,375 A | * | 9/1996 | Ewall | 602/58 |
| 5,562,107 A | | 10/1996 | Lavender et al. | |
| 5,817,145 A | | 10/1998 | Augustine | |
| 5,947,914 A | | 9/1999 | Augustine | |
| 5,954,680 A | | 9/1999 | Augustine | |
| 5,961,480 A | | 10/1999 | Augustine | |
| 5,964,721 A | | 10/1999 | Augustine | |
| 5,964,723 A | | 10/1999 | Augustine | |

(Continued)

FOREIGN PATENT DOCUMENTS

DE    37 16575 A1    12/1988

(Continued)

OTHER PUBLICATIONS

Davey publication description of Allevyn at the time of the Mills invention and applicant's invention, p. 1.*

(Continued)

*Primary Examiner*—Melanie J Hand
(74) *Attorney, Agent, or Firm*—Terrance A. Meador; INCAPLAW (57) ABSTRACT

A tissue treatment device has a flexible treatment portion that includes one or more parts and holes arranged in an openwork. A treatment area is defined in the openwork. The treatment portion is deployed such that the treatment area is positioned over tissue to be treated. The openwork minimizes contact between the tissue treatment device and the tissue being treated. A flexible cover is secured against the flexible treatment portion to close the holes and form a treatment volume in the openwork. The minimal contact between the tissue treatment device and the tissue being treated promotes a desired clinical objective.

45 Claims, 10 Drawing Sheets

U.S. PATENT DOCUMENTS

| | | | |
|---|---|---|---|
| 5,986,163 A | 11/1999 | Augustine | |
| 6,010,527 A * | 1/2000 | Augustine et al. | 607/96 |
| 6,051,747 A * | 4/2000 | Lindqvist et al. | 602/46 |
| 6,093,160 A | 7/2000 | Augustine et al. | |
| 6,110,197 A | 8/2000 | Augustine et al. | |
| 6,510,634 B1 * | 1/2003 | Riley | 40/633 |

FOREIGN PATENT DOCUMENTS

| | | |
|---|---|---|
| DE | G 89 02 311.0 | 6/1989 |
| DE | 198 25 577 A1 | 12/1999 |
| EP | 0 745 365 A2 | 12/1993 |
| EP | 0 424 165 B1 | 5/1994 |
| EP | 424165 B1 * | 5/1994 |
| EP | 0 256 893 B1 | 6/1994 |
| EP | 0 486 522 B1 | 12/1994 |
| EP | 0 982 015 | 11/1995 |
| EP | 0 745 365 B1 | 12/1996 |
| EP | 397 096 B1 | 7/2005 |
| FR | 1 121 037 | 7/1956 |
| GB | 2 288 334 A | 10/1995 |
| GB | 2288334 A * | 10/1995 |
| WO | WO 98/46179 | 10/1998 |
| WO | WO 02/089718 A3 | 11/2002 |

OTHER PUBLICATIONS

Notification of Transmittal of the International Search Report or the Declaration, PCT International Search Report for PCT/US02/14804, dated Mar. 21, 2003.
Einspruch gegen EP 1 397 096 B1, Date Apr. 24, 2006.
Opposition to EP 1 397 096 B1, Date Apr. 24, 2006 (English translation of Einspruch gegen EP 1 397 096 B1).
Einspruch gegen EP 1 397 096 B1, Date Jan. 29, 2007.
Letter from the Opponent in EP 1 397 096 B1, Date Jan. 29, 2007 (English translation of Einspruch gegen EP 1 397 096 B1 dated Jan. 29, 2007).

* cited by examiner

MINIMAL CONTACT TREATMENT DEVICE

PRIORITY

This patent application claims priority from U.S. Provisional Patent Application No. 60/290,266, filed May 10, 2001.

CROSS REFERENCE TO RELATED APPLICATION

This patent application contains material related to the subject matter of U.S. patent application Ser. No. 09/476,554; filed Jan. 3, 2000, for "Modular Bandage."

BACKGROUND OF THE INVENTION

The invention is in the field of medical devices used, adapted, or constructed to treat tissue, such as skin. Especially, the invention is a treatment device for application to tissue for treatment of the tissue. For example, the invention concerns the treatment of wounds with a treatment device that minimizes the area of the wound that is contacted by the device.

U.S. Pat. Nos. 5,817,145; 5,947,914; 5,954,680; 5,961,480; 5,964,721; 5,964,723; 5,986,163; 6,010,527; 6,093,160; 6,110,197; and many others, all assigned to Augustine Medical, Inc. describe treatment devices that attach to the skin and surround an area of tissue to be treated without contacting the tissue to be treated. The devices all form a controlled treatment environment over the tissue to be treated. Parameters or elements of the treatment environment such as moisture, heat, and medicaments are controlled within the treatment volume. This produces manifold beneficial effects such as accelerated wound healing, pain relief, and reduction of infection.

It nevertheless is the case that, because of varying circumstances, not all tissue on a human or animal body can be easily treated with these treatment devices. For example, it is difficult to treat large wounds on contoured dermal surfaces, without contacting the wounds. Such contact, however, is undesirable because movement or removal of the treatment device can rip out healing tissue. Further, moisture tends to collect where contact occurs, macerating the tissue.

The problem is therefore to provide a tissue treatment device configured or constructed to maintain a controlled treatment environment about tissue to be treated which is a large and/or contoured site, while minimizing contact between the tissue treatment device and the tissue being treated.

SUMMARY OF THE INVENTION

The solution to the problem is a tissue treatment device including a flexible treatment portion with a first surface and a second surface and a plurality of openings between the first surface and the second surface, the openings and one part or a plurality of parts of the tissue treatment device forming an openwork in a treatment area of the tissue treatment device with a minimum of surface to contact tissue being treated. A cover is receivable against the first surface, and one or more adhesive portions may be provided to secure the cover over the first surface to form a treatment volume in the openwork.

The treatment area may be defined by a boundary on one of the first and second surfaces that circumscribes the openings. In this case, one or more parts of the flexible treatment portion will be in the treatment area and the magnitude ($A_T$) of the treatment area will be related to the magnitude ($A_O$) of an aggregate area of the openings by $A_T > A_O$.

An important objective of this invention is therefore to provide a tissue treatment device for application to tissue which provides a controlled treatment environment for tissue to be treated, while minimizing the amount of the tissue to be treated that is contacted by the device.

This objective, and many other objectives and advantages are achieved by the tissue treatment device of this invention, as will be manifest when the following detailed description is read with reference to the drawings described below.

BRIEF DESCRIPTION OF THE DRAWINGS

FIGS. 1A-1E illustrate an embodiment of the tissue treatment device according to the invention, in which

FIGS. 2A-2C illustrate another embodiment of the tissue treatment device, in which

FIGS. 3A-3C illustrate another embodiment of the treatment tissue device, in which

FIGS. 4A-4D illustrate another embodiment of the tissue treatment device, in which

FIGS. 7A-7D illustrate use of a heater assembly with the tissue treatment device, in which

DETAILED DESCRIPTION OF THE PREFERRED EMBODIMENTS

The figures illustrate various embodiments and details of a novel tissue treatment device having a construction for application to large and/or contoured areas of a human or an animal while maintaining a controlled, minimally contacting treatment environment against tissue where the device is applied. For example, consider a skin graft donor site that may substantially encompass the circumference of a person's thigh. A structure to conveniently support a cover that maintains a controlled treatment environment about the site will have to touch the site in order to keep the cover in position over the site. The invention provides such support, while minimizing the amount of tissue in the site that is contacted.

The invention is, broadly, a tissue treatment device. Other terms related to particular applications might be used to name or describe the invention. Such terms may include "bandage", "plaster", "covering", and so on. Use of such terms is not meant to limit the scope or application of the invention.

In addition, the invention is intended to be used to apply a controlled treatment environment over or against tissue in order to treat the tissue. The tissue being treated by the invention may include wounds, potential wounds, grafts, pre- and post-surgical sites, healthy tissue, diseased tissue, wounded or insulted tissue, dermal and subdermal locations, and so on. Such applications are not intended to limit the scope or use of the invention.

The tissue treatment device is composed of flexible elements that permit the elements, and the device, to be deployed over contoured surfaces and limbs.

Figure 1A:
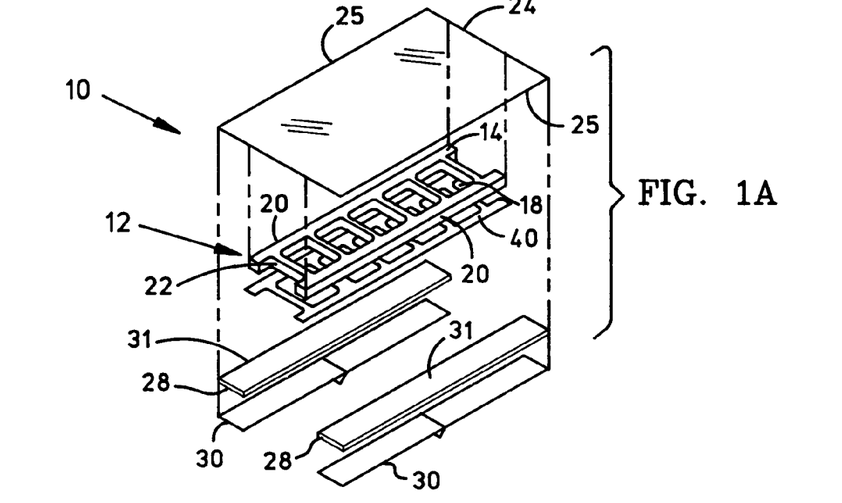
FIG. 1A is an exploded perspective assembly drawing of the tissue treatment device.
Figure 1B:
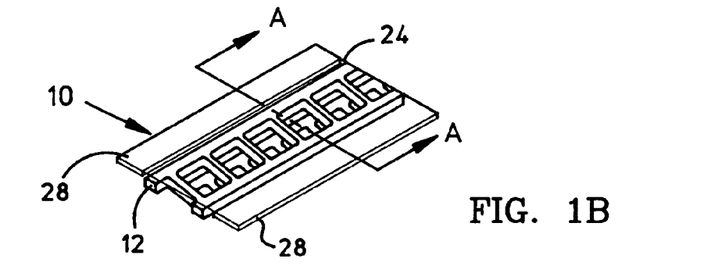
FIG. 1B is a perspective view of the assembled tissue treatment device.
Figure 1C:
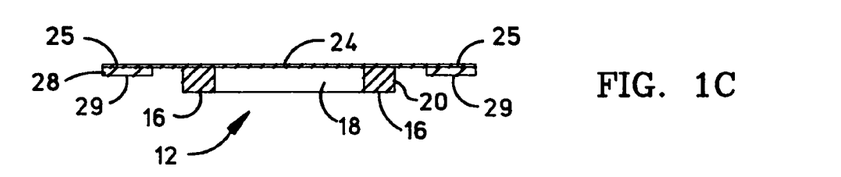
FIG. 1C is a side sectional view of the tissue treatment device taken along lines A-A in FIG. 1B.
Figure 1D:
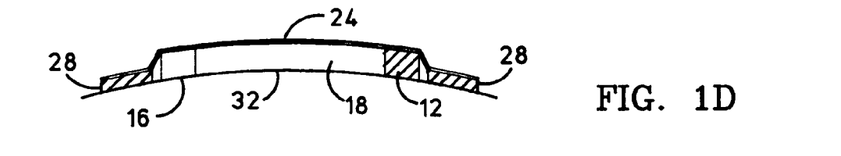
FIG. 1D is the side sectional view of FIG. 1C after the tissue treatment device is deployed for use.

Refer now to FIGS. 1A-1E for an understanding of one embodiment of the invention. In these figures, a tissue treatment device 10 includes a flexible treatment portion 12 having a first surface 14 and a second surface 16 (which is best seen in FIGS. 1C and 1D). In these figures, the first surface 14 has the function of supporting a cover over or against the flexible treatment portion 12. The second surface 16 is intended to be oriented to face tissue to be treated by the device. If the flexible treatment portion 12 is reversible, which is within the scope of the invention, each surface can perform either function.

Figure 1E:
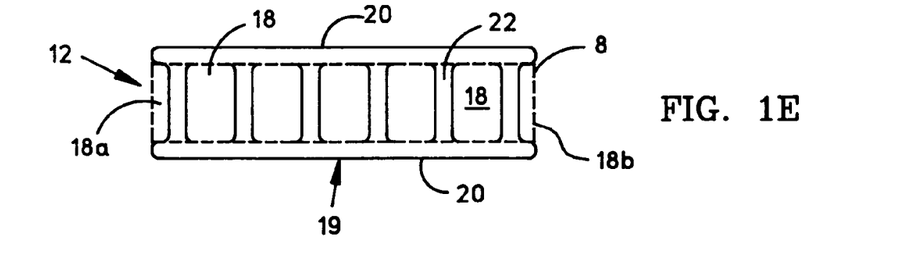
FIG. 1E is a plan view of a major surface of the tissue treatment device in which a boundary defines a treatment area.

A plurality of holes, spaces, or openings 18 extend through the flexible treatment portion 12, between the first and second surfaces 14, 16, forming an openwork 19 (FIG. 1E. This element may also be called a "latticework".). More particularly, the structure of the flexible treatment portion 12 includes one or more parts arranged in a repeating pattern to present a unit hole or opening 18 that repeats periodically in the structure of the flexible treatment portion 12. In the embodiment of these figures, the one or more parts include lateral members 20 that are disposed in parallel, separated by parallel cross pieces 22 oriented transversely to, and arranged in a repeating pattern between, the lateral members 20. All of the parts are connected and, in this embodiment, form the holes, spaces, or openings 18 in a repeating, linear sequence.

The holes, spaces, or openings 18 of this embodiment have a repeating unit with a quadrilateral shape. This is not meant to limit the invention to having an openwork with a single repeating pattern, or to an openwork with just a quadrilateral hole shape. Many other patterns are possible in such an openwork; many other shapes are also possible, including, without limitation, rounded, polygonal, star, regular, and irregular.

A flexible cover 24, embodied for example as a film of plastic material, is received over or against the first surface 14 (or the second surface 16, if the flexible treatment portion 12 is reversing). The flexible cover 24 may have an extent that is sufficient to lie over and close ends of some or all of the holes, spaces, or openings 18 in the openwork 19 in order to form a treatment volume therewith in the flexible treatment portion 12 when received over or against one of the two surfaces 14, 16. In this embodiment, the flexible cover 24 is sized to cover all of the holes, spaces, or openings 18 and to extend past the lateral members 20. One or more adhesive portions are provided to secure the flexible cover 24 over or against the first surface 14 (or the second surface 16 if the flexible treatment portion 12 is reversible). In this embodiment, there are two adhesive members 28 disposed against one surface of the flexible cover 24, spaced apart, near lateral edges 25 of the flexible sheet 24. Each adhesive member 28 is a rectangular piece, shaped from a flexible material with two opposing surfaces 29 and 31 that carry adhesive. Alternatively, the surface 31 may be thermally bonded to the flexible cover 24. The adhesive members are made of open foam material which may have one or more surfaces skinned. On each of the adhesive members 28, one of the surfaces 29 may have a release liner 30.

In use, the tissue treatment device 10 may be provided in kit form with the elements described above unassembled. When the tissue treatment device 10 is being assembled for use, the flexible treatment portion 12 is placed on skin, with the openwork 19 deployed over tissue to be treated. It is assumed that the first surface 14 and the second surface 16 are disposed as illustrated in FIGS. 1A-1D, although they may be reversed if the flexible treatment portion 12 is reversible. The flexible cover 24 is placed over or against the first surface 14, with its edges 25 extending beyond the lateral members 20. The adhesive members 28 are applied, each by an exposed adhesive surface, to the surface of the flexible cover 24 that faces the first surface 14, near the edges 25. The release liners 30 are removed, and the surfaces 29, with exposed adhesive, are brought against skin, thereby securing the flexible cover 24 over the first surface 14. The tissue treatment device 10 is illustrated in assembled form in FIGS. 1B, 1C, and 1D. As FIGS. 1C and 1D, show, the flexible cover 24 forms a treatment volume with holes, spaces, or openings 18 when brought over or against the first surface 14. The flexible cover 24 is shown secured over or against the first surface 14 in FIG. 1D, with a treatment volume in the holes, spaces, or openings 18 disposed against a portion 32 of the tissue being treated.

There are alternative possible configurations that may be applied to the elements of the tissue treatment device thus far described. These can be understood with further reference to FIGS. 1A-1E. For example, the flexible treatment portion 12 and the flexible cover 24 may be partially assembled by bonding the first surface 14 and the flexible cover 24 by gluing, thermal processing, or ultrasonic processing. This would provide the flexible treatment portion 12 and the flexible cover 24 as a single unit. In this case, the portions of the flexible cover that extend beyond the lateral members 20 could be eliminated and the adhesive portions 28 could be disposed on the portions of the second surface 16 occupied by the lateral members.

Minimization of contact between the tissue treatment device 10 and tissue being treated can be appreciated with reference to FIG. 1E, which is a plan view of the flexible treatment portion 12. The openwork 19 is visible and, with it, all of the holes, spaces, or openings 18, including hole, space, or opening portions 18a and 18b at respective ends of the flexible treatment portion 12. The portion of the openwork 19 that contains all of the holes, spaces, or openings 18 and the portions 18a and 18b is circumscribed by a boundary B. The inside of the boundary B is a treatment area of the tissue treatment device 10 that is intended to face, lie against, or contact tissue to be treated. The treatment area has a magnitude ($A_T$) in square units. Included in the treatment area is at least one part of the one or more parts of the flexible treatment portion 12. For example, cross pieces 22 are in the treatment area illustrated in FIG. 1E. These are the structural elements of the tissue treatment device that will contact the tissue being treated. One way to appreciate how the use of an openwork structure can minimize such contact is to consider a relationship between the magnitude in square units ($A_O$) of the aggregate area of the holes, spaces, or openings 18 and portions 18a and 18b and the magnitude ($A_T$) of the treatment area, in which the aggregate area of the holes, spaces, or openings is always less than the treatment area. In this case, the remainder of the treatment area that is not in the aggregate area of the holes, spaces, or openings is distributed over the one or more parts of the flexible treatment portion that are in the treatment area. The relationship can be expressed as $A_T > A_O$.

Returning to the description of the first embodiment of the tissue treatment device illustrated in FIGS. 1A-1E, the flexible treatment portion functions as a standoff having a shape and a treatment area sufficient to lie over an area of tissue to be treated that elevates the flexible cover 24 above and out of contact with the area of tissue being treated. The flexible treatment portion 12 is formed or fabricated, for example, from an absorbent foam to support autolytic debridment. Further, the flexible treatment portion 12 may be impregnated with a medicament including an antibiotic, antifungal, or antimicrobial agent. The flexible cover 24 is a sheet or film of material that may have a moisture vapor transmission rate (MVTR); its purpose is to create a breathable, controlled treatment environment in the treatment volume it forms with the holes, spaces, or openings 18 and portions 18a and 18b. The sheet may also be impregnated with antimicrobial agents. Descriptions of materials from which the flexible treatment portion 12 and the flexible cover 24 may be made are found in U.S. patent application Ser. No. 09/476,554, filed Jan. 3, 2000, entitled "Modular Bandage", which is assigned in common with this application and incorporated herein by this reference.

Presuming that the flexible treatment portion 12 is made of foam, or an equivalent absorbent material, it is desirable in some cases to control or modulate the passage of moisture through a surface of the flexible treatment portion 12 that contacts the tissue being treated, in order to discourage the accumulation of moisture at the interface between the surface and tissue, which could cause maceration of the tissue at that interface. To control the passage of moisture through a tissue-contacting surface of a flexible treatment portion made of foam, and also to retard the growth of tissue into the open cells of the material, the surface can be skinned, either by heating and pressurization of the surface, or by applying a layer or film of material. Such skinning or material can be impermeable, or can have a permeability that is different (for example, less) than that of the open cell foam material. Such a layer is indicated by reference numeral 40 in FIG. 1A. Manifestly, either or both of the surfaces 14 and 16 could be skinned. If both surfaces are skinned (or if neither is skinned) the flexible treatment portion 12 would be reversible in that it could be oriented such that either of the surfaces 14 and 16 could face the tissue being treated.

Other possible amendments or enhancements of the tissue treatment device of this invention include the application of a lightly tacky adhesive substance to the surface of the flexible treatment portion that faces the tissue being treated. Such an adhesive could be selected from the group including silicone gel, petroleum jelly, hydrogel and hydrocolloid. Such an adhesive would further stabilize the tissue treatment device over tissue being treated, at the same time that it slightly cooled the tissue. Further, the adhesive members 28 could be replaced with layers or films of acrylic adhesive materials.

Other embodiments of the tissue treatment device and its elements will now be illustrated and described. These illustrations and descriptions will not include all of the details, variations, and possible alternative materials, structures and assemblies that have been presented in detail in the description of the embodiment of FIGS. 1A-1E. Nevertheless, it will be understood that any or all such detail may also apply to the following embodiments.

Figure 2A:
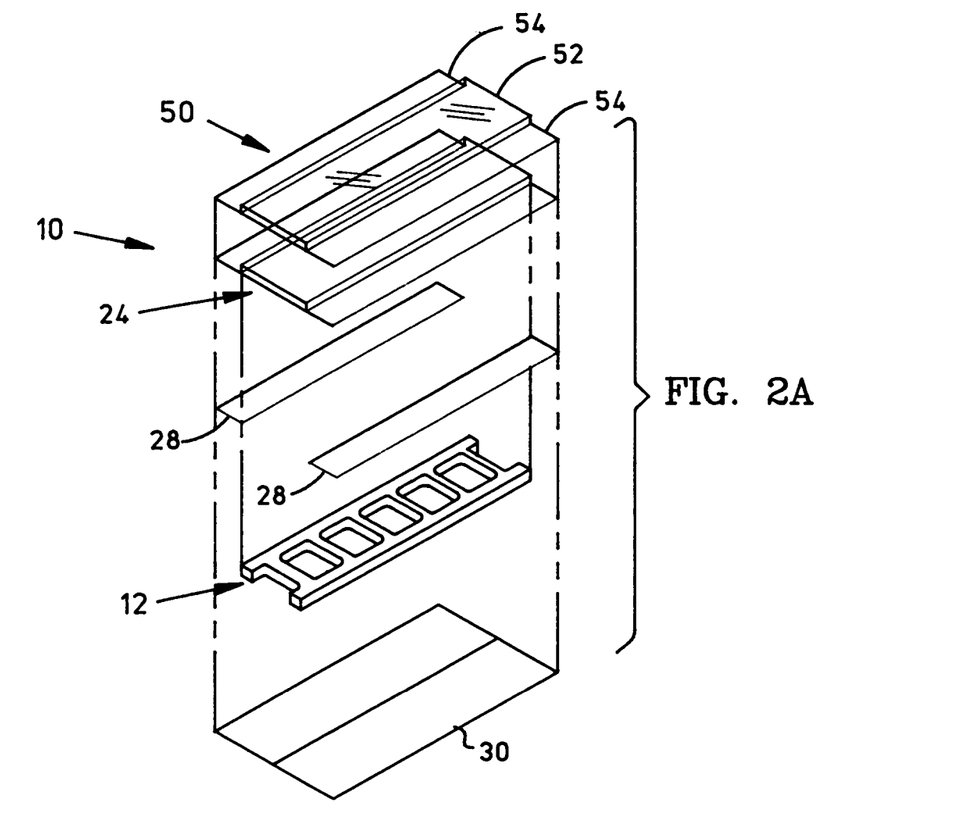
FIG. 2A is a an exploded perspective assembly drawing of the tissue treatment device.
Figure 2B:
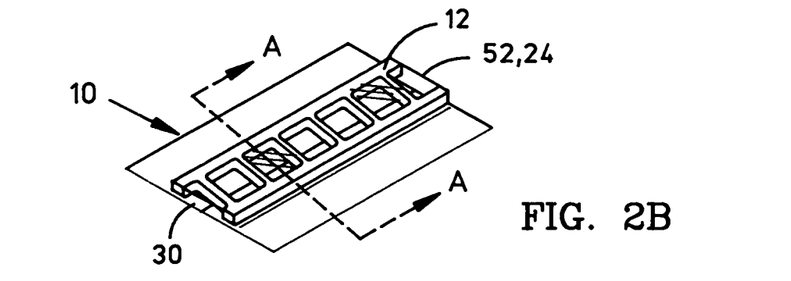
FIG. 2B is a perspective view of the assembled tissue treatment device.
Figure 2C:
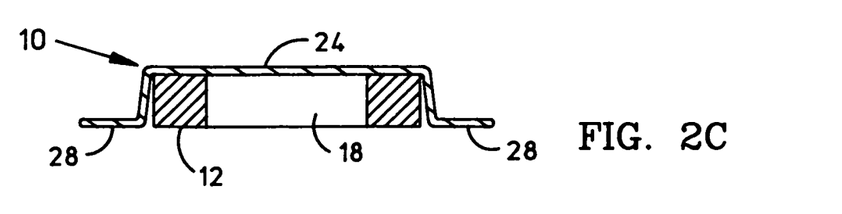
FIG. 2C is a side sectional view taken along the lines A-A in FIG. 2B.

FIGS. 2A-2C illustrate the tissue treatment device 10 already described in connection with FIGS. 1A-1E with an additional element, a delivery piece 50. The delivery piece 50 has a raised portion 52 and lateral portions 54. The raised portion 52 and lateral portions 54 define a rectangular space that receives the flexible cover 24 and the flexible treatment portion 12, and contains or retains them loosely for handling and application. In this regard, there may be circumstances in which it would be desirable for the flexible cover 24 to be very thin and light. Presume, for example that the flexible cover 24 is a thin, highly flexible film of urethane and the adhesive members 28 are thin layers or films of acrylic adhesive material. Such a structure would be difficult to handle and apply. In such a case, the flexible cover 24 may be cast into the delivery piece 50. For example, the delivery piece 50 may be made of a material having enough rigidity to maintain the rectangular space while the tissue treatment device is being handled and applied, but enough flexibility to adapt to the contour of tissue to be treated. Examples of such material include polyethylene, polyester, and a fibrous material such as the paper used in release liners for adhesive films. The flexible cover 24 (with adhesive films 28 and single release cover 30 applied) would be received in the rectangular space of the delivery piece 50. The flexible treatment portion 12 would also be received in the rectangular space, sandwiching the flexible cover 24 between itself and the raised portion 52. The adhesive layers or films 28 would be positioned under the lateral portions 54 of the delivery piece 50. This would impart enough rigidity to the tissue treatment device for handling, removal of the release liner 30, and application of the tissue treatment device 10, with the adhesive films 28 retaining the tissue treatment device against skin. The delivery piece 50 would then be removed from the tissue treatment device 10.

Figure 3A:
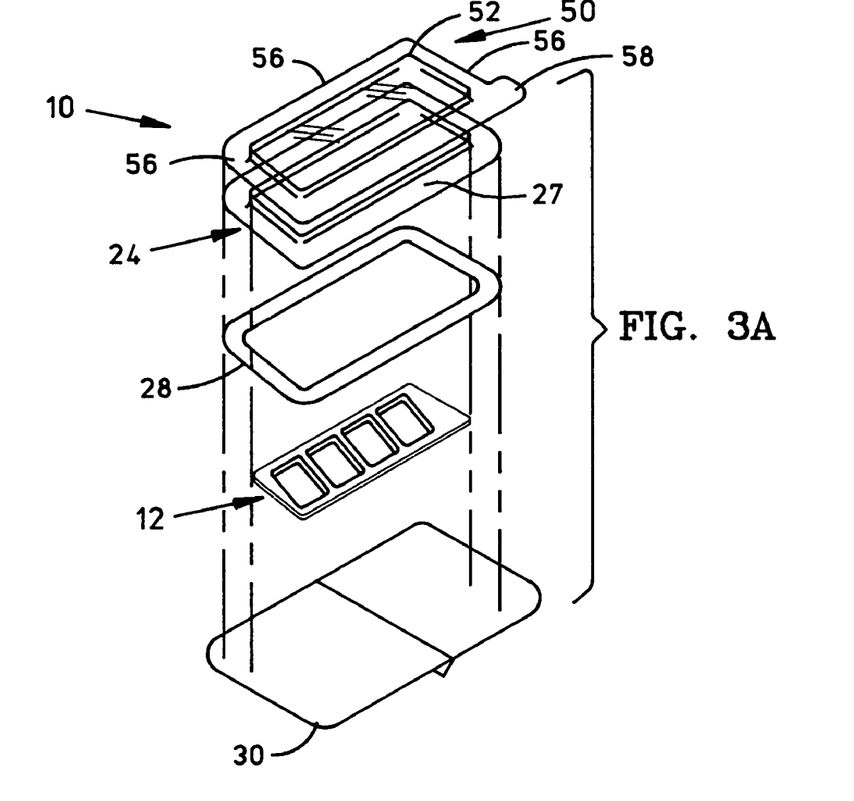
FIG. 3A is an exploded perspective assembly drawing of the tissue treatment device.
Figure 3B:
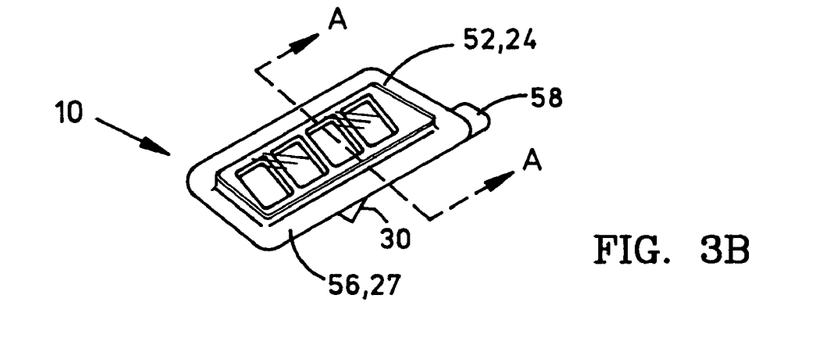
FIG. 3B is a perspective view of the assembled device.
Figure 3C:
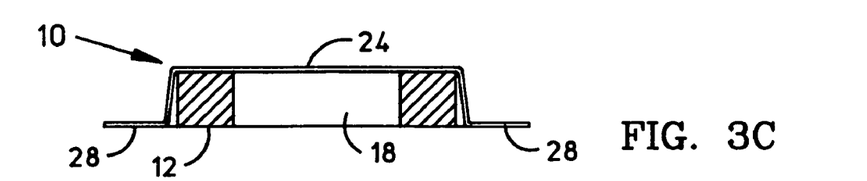
FIG. 3C is a side sectional view taken along lines A-A in FIG. 3B.

FIGS. 3A-3C illustrate another embodiment of the tissue treatment device 10 with a delivery piece 50 having a raised portion 52 defining a rectangular space and a continuous skirt, border, or outer edge 56 with a pull tab 58. This delivery piece 50 may be thermally formed or cast using a polyolefin or other equivalent thermoplastic material. The flexible cover 24 may be applied to the delivery piece 50 prior to the shaping or forming of the piece. In this case, the flexible cover 24 takes on the shape of the delivery piece 50, with a continuous skirt 27 on the lower surface of which is disposed a corresponding layer or film of acrylic adhesive 28. In this case, the release liner 30 may have a shape that fills in the space within the skirt 27. In addition, the flexible treatment portion has closed ends so that all of the holes, spaces, or openings 18 have complete, closed outlines.

Figure 4A:
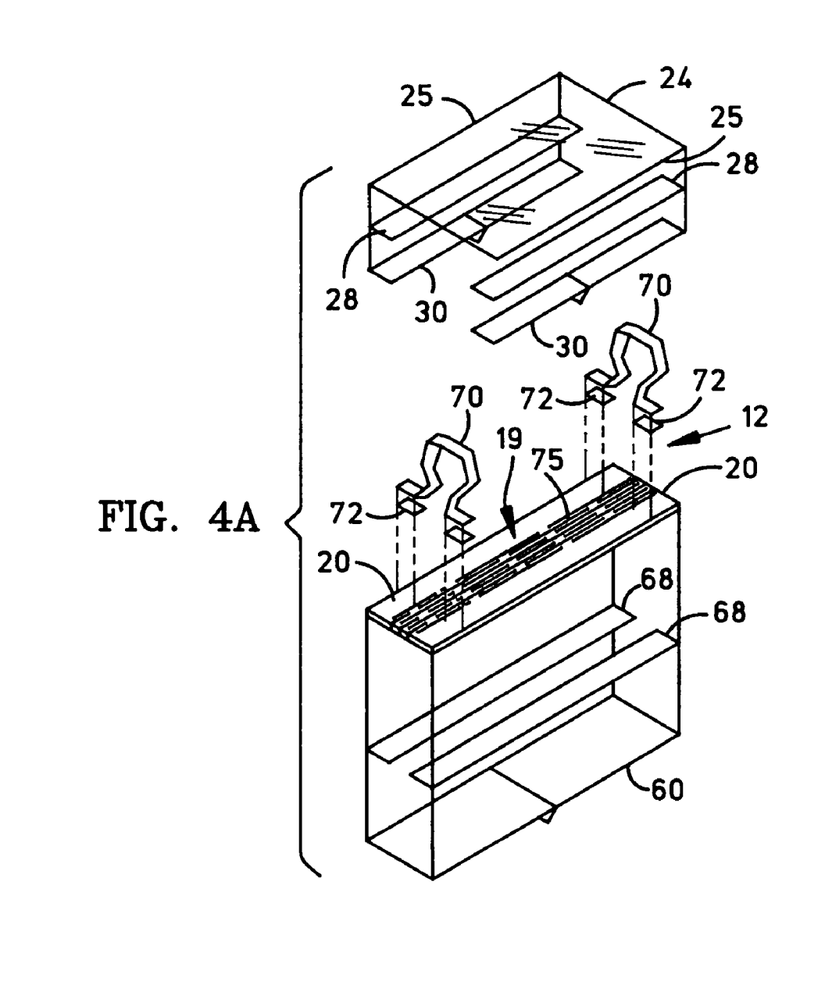
FIGS. 4A, 4B and 4C are exploded perspective assembly drawings.
Figure 4B:
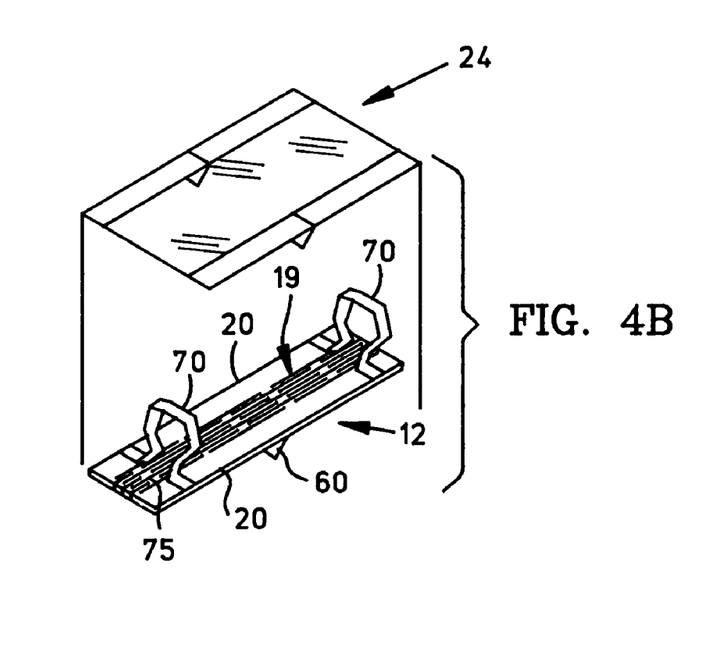
Figure 4C:
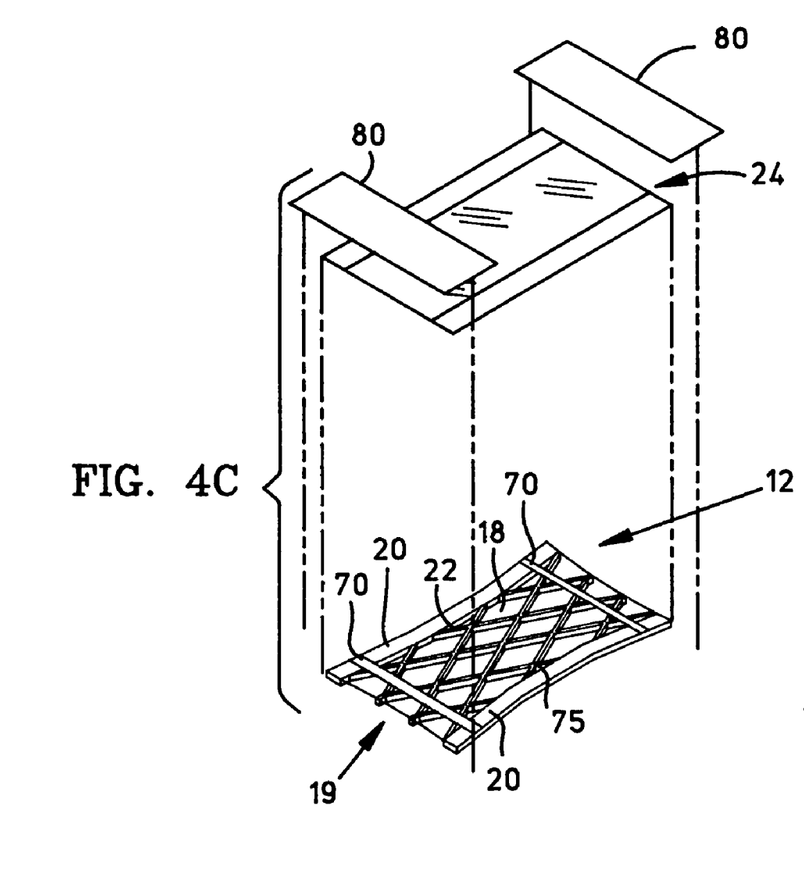
Figure 4D:
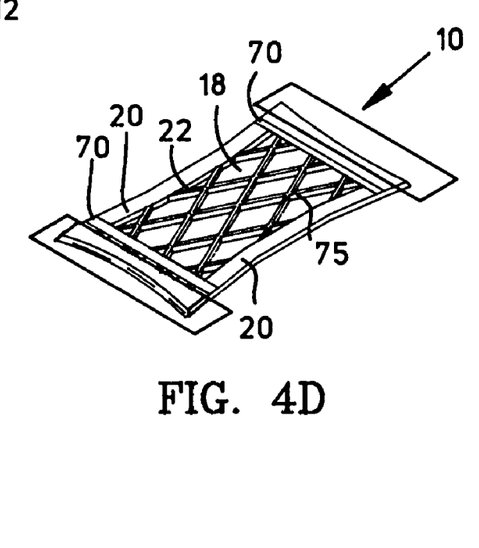
FIG. 4D is a perspective view of the tissue treatment device in use.

FIGS. 4A-4D illustrate an embodiment of the tissue treatment device 10 where the openwork 19 is provided in a moveable lattice 75 in which the cross pieces 22 are arranged in a repeating pattern forming a unit hole or opening having a diamond shape. In this embodiment, the lateral members 20 are initially brought together, with the moveable lattice 75 compressed between them. Retention strips 70, attached at their ends to the lateral members 20 by adhesive films 72, are initially flexed (FIGS. 4A and 4B) when the latticework 75 is compressed. As shown in FIGS. 4C and 4D, when the treatment member 12 is deployed for use, the lateral members 20 are separated, the latticework 75 opens to present the openwork 19, and the retention strips 70 play out to their full extent, retaining the treatment portion 12 in a maximally expanded configuration. In this embodiment, adhesive layers or films 28, with corresponding release liners 30, are provided on the lower surface of the flexible cover 24, near the edges 25. Similarly, adhesive layers or films 28 are provided on the portion of the second surface 16 occupied by the lateral members 20, with a single release liner 60. Additionally, end anchor sheets 80, with adhesive on their lower surfaces are used to secure the ends of the tissue treatment device 10 embodiment of FIGS. 4A-4D. End anchor sheets 80 may perform similar functions for other embodiments described herein.

Figure 5A:
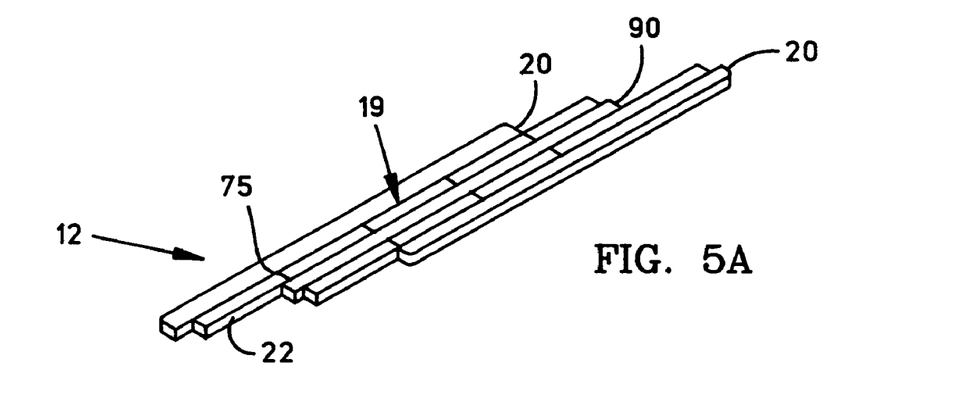
FIGS. 5A-5C illustrate an embodiment of a flexible treatment portion of the tissue treatment device with a moveable latticework.
Figure 5B:
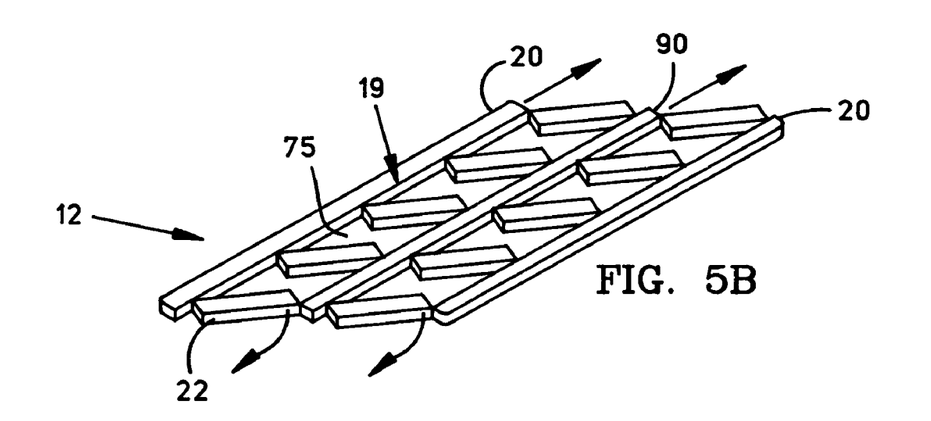
Figure 5C:
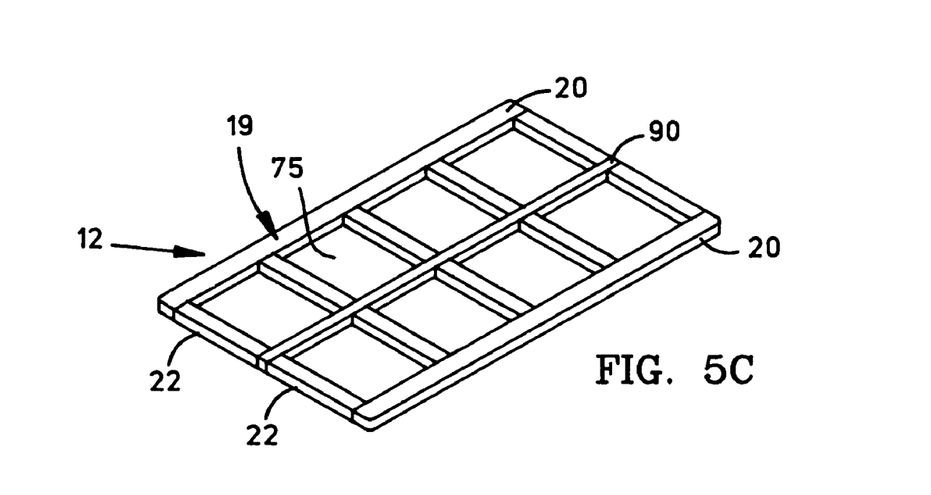

FIGS. 5A-5C illustrate another embodiment of the treatment portion in which the openwork 19 is provided in a moveable latticework 75. In this embodiment, a central member 90 is positioned between and parallel to the two lateral members 20. Each of the cross pieces 22 is pivotally connected at one of its ends to one of the lateral members 20 and at its other end to the central member 90. This permits the lateral members 20 and the central member 90 to move away (and together) to open (or close) the latticework 75 in which the members 20 and 90 and the cross pieces 22 are arranged in a repeating pattern forming a unit hole or opening having a rectangular shape.

Figure 6A:
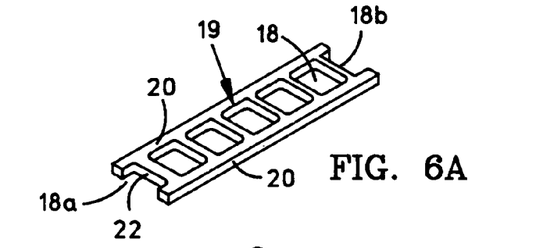
FIGS. 6A-6F illustrate embodiments of the flexible treatment portion of the tissue treatment device.
Figure 6B:
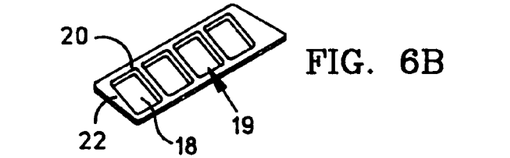
Figure 6C:
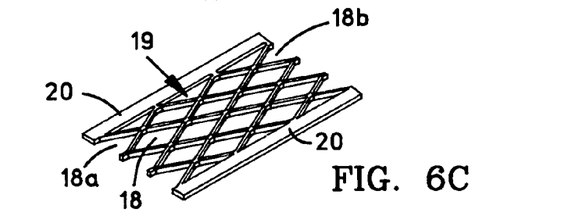
Figure 6D:
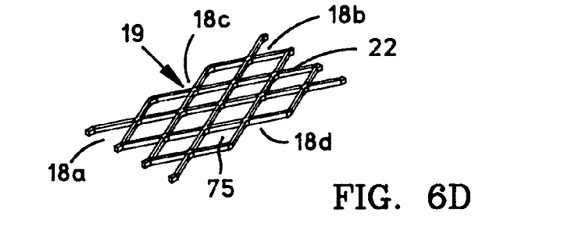
Figure 6E:
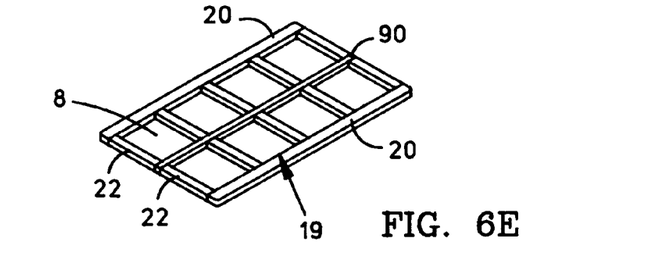
Figure 6F:
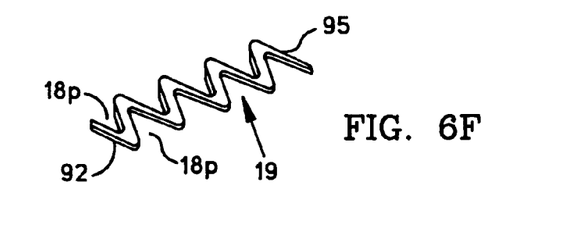
Figure 7A:
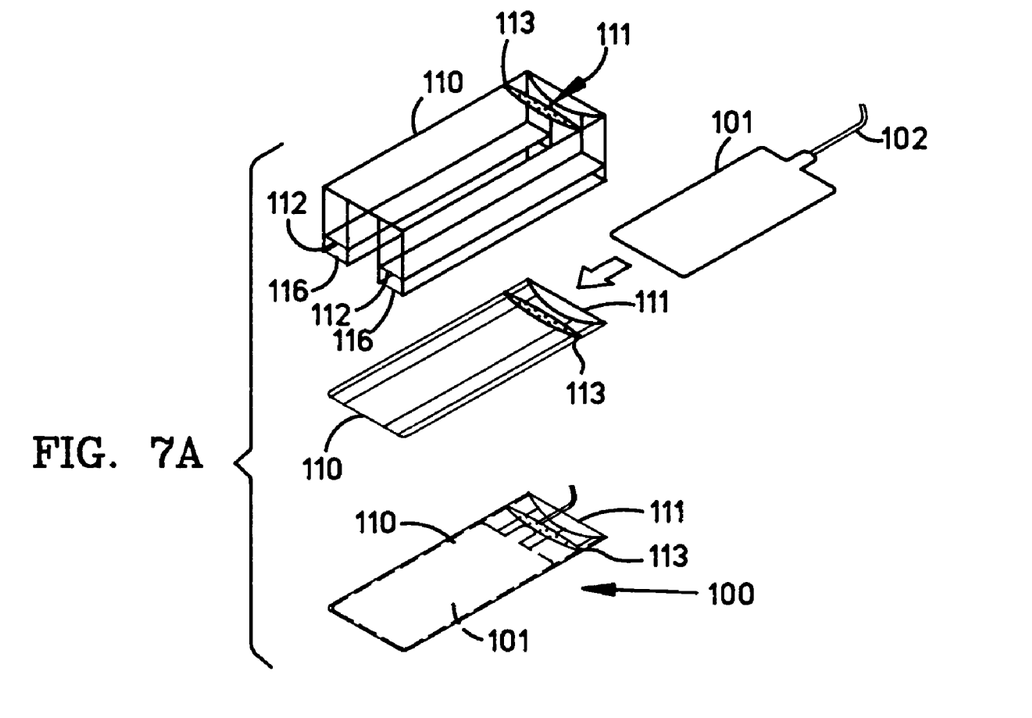
FIG. 7A is an exploded perspective assembly drawing of the heater assembly.
Figure 7B:
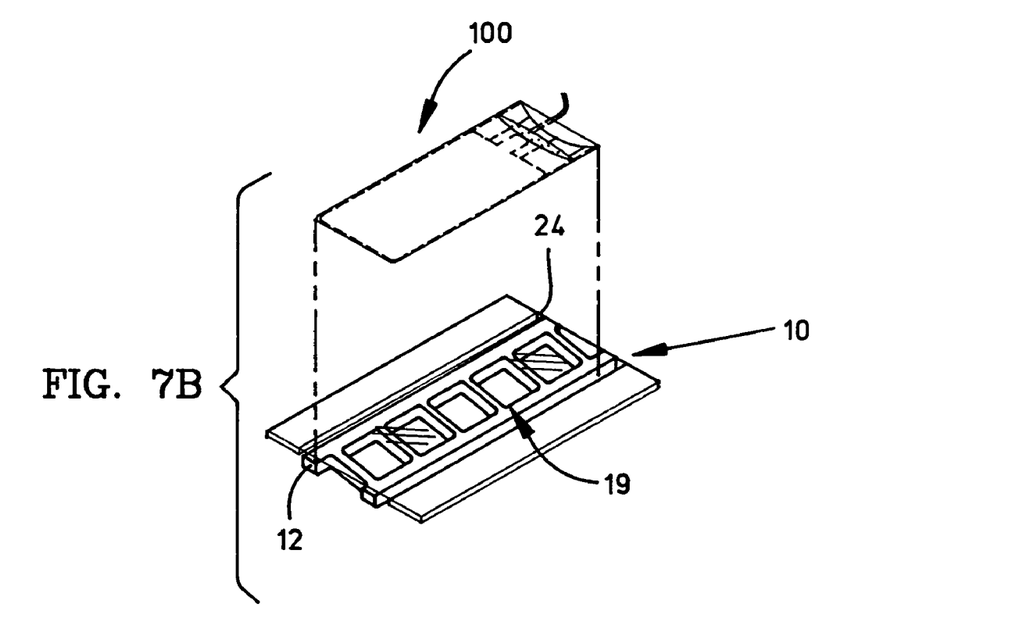
FIG. 7B is a perspective assembly view showing attachment of the heater assembly to the tissue treatment device.
Figure 7C:
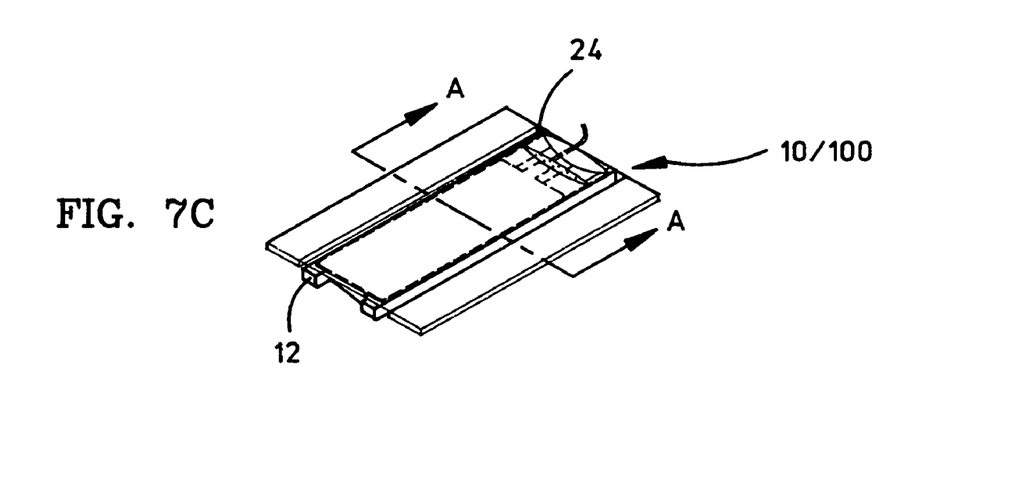
FIG. 7C is a perspective view of the heater assembly assembled to the tissue treatment device.
Figure 7D:
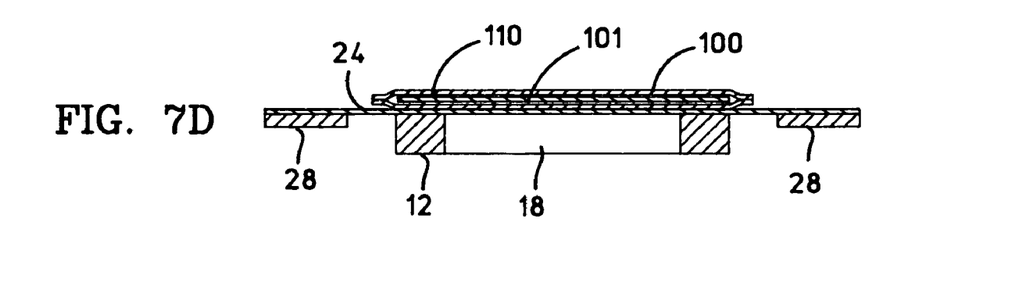
FIG. 7D is a side sectional view taken along A-A of FIG. 7C.

FIGS. 6A-6C and 6E illustrate the embodiments of the treatment portion 12 that have been illustrated and specified. All include the openwork 19 formed by a plurality of holes, spaces, or openings 18; the holes, spaces, or openings 18 are defined by parts arranged in repeating patterns. Some of the openwork embodiments are moveable, some are not. FIG. 6D shows an embodiment of the flexible treatment portion 12 in which the openwork 19 is rendered by a latticework 75 formed entirely of crosspieces 22. FIG. 6F illustrates an embodiment of the flexible treatment portion 12 having a single part 95 formed into a sinuous pattern that defines holes, spaces, or openings 18p that are not complete, closed patterns; this embodiment may be rendered by a single part formed into any one of a number of wavelike patterns in which the basic repeating pattern of the part could form holes, spaces, or openings having sawtooth, triangular, square, rectangular, and other equivalent shapes. Similarly, the openings of the flexible treatment portion 12 of FIG. 6F could be formed as complete holes, spaces, or openings with closed perimeters in a single part.

A heater is an optional element of a tissue treatment device according to this invention. The optional heater can be active or passive. An active heater is an exothermic device, while a passive heater is a reflective or an insulating device. In either case, the purpose of the heater is to control the temperature element of the controlled treatment environment provided by the tissue treatment device 10, for example, by maintaining a temperature in or near the controlled treatment environment in a normothermic range. The heater can be attached directly to, or disposed in or under the flexible cover 24. In any case, the heater is disposed over or aligned with the controlled treatment volume of the tissue treatment device. FIGS. 7A-7D illustrate a heater embodiment. This embodiment is illustrative of but one possible way of applying a heater to the tissue treatment device 10. The heater in these figures is an exothermic heater in which heat is generated by electro-resistive operation. This is not intended to so limit any heater that might be used with the tissue treatment device 10. Other exothermic heaters, for example, could generate heat by chemical reactions or by the flow of a heated medium. These figures show a heater assembly 100 including a flexible, elongate, rectangular electro-resistive heating element 101, with a power lead 102, received in a heater support that includes a flexible plastic pocket, container, or envelope 110. The pocket, container, or envelope 110 has an open end 111 with a mechanism 113 for releasably locking the open end 111 when the heating element has been received in the pocket, container, or envelope 110. In addition, adhesive portions 112, with corresponding release liners 116, are received on one surface of the pocket, container, or envelope 110. The heater assembly 100 can be attached to the tissue treatment device 10, over the openwork 19, by removing the release liners 116, and placing the pocket, container, or envelope 110, with the heating element 101 in it, on the flexible cover 24, where it can be removably retained by the adhesive portions 112.

Figure 8:
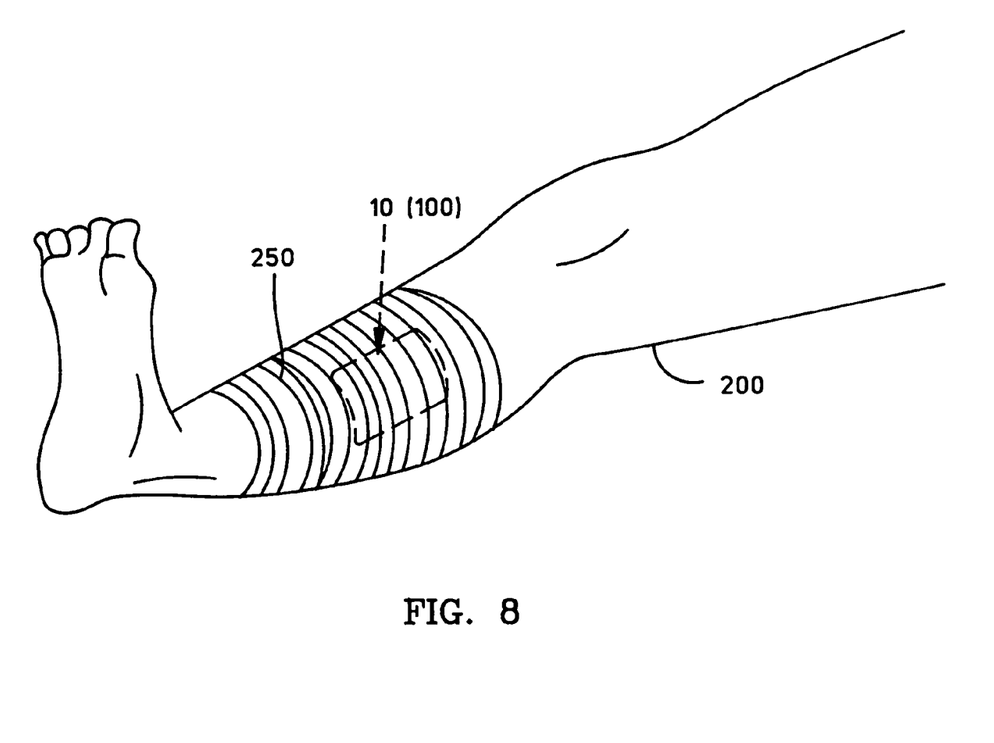
FIG. 8 is a perspective view of the human limb on which the tissue treatment device has been deployed in combination with a compression bandage.

FIG. 8 illustrates application of the tissue treatment device 10 (with or without a heater) in combination with a pressure bandage 250 on a limb 200 (lower leg). The tissue treatment device 10 is deployed over tissue to be treated (not seen in the figure) as described above. The pressure bandage 250 is then wrapped around the limb 200, over the tissue treatment device 10.

The tissue treatment device thus described and illustrated may be used with a single flexible treatment portion for treatment of an expanse of tissue, or with one or more adjacent or proximate flexible treatment portions made according to the invention and used as described in this specification.

Those skilled in the art will realize that the tissue treatment device illustrated and described herein can be varied in form and construction according to many circumstances without departing from the scope of the claims that follow.

We claim:

1. A treatment device, comprising:
a delivery piece with a raised portion and lateral portions defining a rectangular space;
a flexible treatment portion with a first surface, a second surface to contact tissue being treated, and one part with a sinuous shape defining a repeating, linear sequence of openings;
the openings extending through the treatment portion from the first surface to the second surface;
a sheet of flexible material received against the first surface and forming a treatment volume with the plurality of openings; and,
one or more adhesive portions to secure the sheet of flexible material over the first surface;
the sheet of flexible material and the treatment portion being received within the rectangular space such that the sheet of flexible material is sandwiched between the flexible treatment portion and the raised portion;
the delivery piece being removable from the sheet of flexible material and the treatment portion when the flexible treatment portion contacts the tissue being treated.

2. The treatment device of claim 1, the treatment portion being absorptive and the second surface being impermeable.

3. The treatment device of claim 1, the treatment portion including an absorptive material.

4. The treatment device of claim 3, the absorptive material being an open cell foam in which the second surface is impermeable.

5. The treatment device of claim 1, the treatment portion being absorptive.

6. The treatment device of claim 1, the treatment portion including an absorptive material.

7. The treatment device of claim 6, the absorptive material being an open cell foam in which the second surface is impermeable.

8. The treatment device of claim 1, the sheet of flexible material including a periphery.

9. The treatment device of claim 8, the one or more adhesive portions including adhesive members to act between the sheet of flexible material near the periphery and tissue.

10. The treatment device of claim 8, the one or more adhesive portions including one or more layers of adhesive to act between the sheet of flexible material near the periphery and tissue.

11. The treatment device of claim 10, the one or more adhesive portions including one or more films of adhesive to act between the sheet of flexible material near the periphery and tissue.

12. The treatment device of claim 1, further including adhesive positioned beneath the lateral portions of the delivery piece to act between the second surface and tissue.

13. The treatment device of claim 1, further including a heater assembly receivable on the treatment device.

14. The treatment device of claim 1 in combination with a pressure bandage.

15. A treatment device, comprising:
   a flexible treatment portion with a first surface, a second surface and one or more parts;
   a plurality of openings opening through the treatment portion, from the first surface to the second surface;
   at least one part and the openings forming an openwork;
   a sheet of flexible material received against the openwork and forming a treatment volume with the plurality of openings;
   adhesive to act between the second surface and tissue; and,
   a single delivery piece with a raised portion and lateral portions defining a rectangular space receiving the sheet of flexible material and the treatment portion and with enough rigidity to maintain the rectangular space while the treatment device is being handled;
   the delivery piece being removable from the sheet of flexible material and the treatment portion when the flexible treatment portion contacts tissue.

16. The treatment device of claim 15, the treatment portion being absorptive and the second surface being impermeable.

17. The treatment device of claim 15, the treatment portion including an absorptive material.

18. The treatment device of claim 17, the absorptive material being an open cell foam with an impermeable surface corresponding to the second surface.

19. The treatment device of claim 15, the at least one part forming a repeating pattern.

20. The treatment device of claim 19, the openings being defined by the at least one part such that the openings include a repeated unit opening in the openwork.

21. The treatment device of claim 15, the one or more parts including at least two lateral parts and a plurality of cross pieces, the cross pieces extending between the two lateral parts, each opening being defined by at least two cross pieces.

22. The treatment device of claim 21, the treatment portion being absorptive.

23. The treatment device of claim 21, the treatment portion including an absorptive material.

24. The treatment device of claim 23, the absorptive material being an open cell foam with a skinned surface corresponding to the second surface.

25. The treatment device of claim 21, the lateral parts being moveable toward and away from each other, the cross pieces forming a moveable openwork.

26. The treatment device of claim 25, the openings being moveable in the openwork.

27. The treatment device of claim 26, the treatment portion being absorptive.

28. The treatment device of claim 26, the treatment portion including an absorptive material.

29. The treatment device of claim 28, the absorptive material being an open cell foam.

30. The treatment device of claim 15, the at least one part and the plurality of openings forming the openwork as a latticework.

31. The treatment device of claim 30, the treatment portion being absorptive.

32. The treatment device of claim 30, the treatment portion including an absorptive material.

33. The treatment device of claim 32, the absorptive material being an open cell foam with a skinned surface corresponding to the second surface.

34. The treatment device of claim 15, the treatment portion including one part with a sinuous shape.

35. The treatment device of claim 15, the treatment portion including one part with a wavelike shape.

36. The treatment device of claim 35, the treatment portion being absorptive.

37. The treatment device of claim 35, the treatment portion including an absorptive material.

38. The treatment device of claim 37, the absorptive material being an open cell foam with a skinned surface corresponding to the second surface.

39. The treatment device of claim 15, the sheet of flexible material including a periphery.

40. The treatment device of claim 39, further including one or more adhesive portions positioned beneath the lateral portions of the delivery piece to secure the sheet of flexible material against the openwork.

41. The treatment device of claim 40, the one or more adhesive portions including adhesive members to act between the sheet of flexible material near the periphery and tissue.

42. The treatment device of claim 40, the one or more adhesive portions including one or more layers of adhesive to act between the sheet of flexible material near the periphery and tissue.

43. The treatment device of claim 42, the one or more adhesive portions including one or more films of adhesive to act between the sheet of flexible material near the periphery and tissue.

44. The treatment device of claim 15, further including a heater assembly receivable on the treatment device.

45. The treatment device of claim 15 further including a pressure bandage.

* * * * *